United States Patent [19]

Kasper et al.

[11] Patent Number: 5,019,513
[45] Date of Patent: May 28, 1991

[54] ANTI-BACTERIAL T-CELL FACTOR

[75] Inventors: Dennis L. Kasper, Newton Center; Dori F. Zaleznik, Newton Highlands; Robert W. Finberg, Roslindale, all of Mass.

[73] Assignee: The Brigham and Women's Hospital, Inc., Boston, Mass.

[21] Appl. No.: 296,849

[22] Filed: Jan. 12, 1989

Related U.S. Application Data

[63] Continuation of Ser. No. 741,232, Jun. 4, 1985, abandoned.

[51] Int. Cl.$^5$ .......................... C12N 5/18; C12P 21/00
[52] U.S. Cl. .............................. 435/240.26; 435/70.2; 435/172.2; 935/105
[58] Field of Search ................... 435/240.26, 68, 172.2, 435/948; 935/90, 101, 105, 107, 109, 111; 530/300

[56] References Cited

PUBLICATIONS

Zalenznik et al., Clinical Res. 31(2):379A (1983).
Whitaker, R. B. and Ruddle, N. H. "Antigen-Specific T Cell Hybrids I. Ovalbumin Binding T Cell Hybrid," Cellular Immunology, vol. 55, No. 1, pp. 56–65, 1980.
Ginsburg, C. H. et al., "Prevention of Granuloma Development in the Mouse by Using T Cell Hybridoma Products," Journal of Immunology, vol. 132, No. 1, pp. 203–208, 1984.
Ziegler et al. (1982), N. E. J. Med. 307:1225–1230.
Shapiro et al. (1982), J. Exper. Med. 154:1188–1197.
Onderdonk et al. (1982), J. Clin. Invest. 69:9–16.
Asherson et al. (1982), Annals. N.Y. Acad. Sci. vol. 392:71–89.
Healey et al. (1983), J. Immunology 131:2843–2847.
Lifshitz et al. (1983), Proc. Nat'l. Acad. Sci. 80:5689–5693.
Murphy et al. (1983), J. Immunol. 130:2876–2881.
Zaleznik et al. (1985), J. Clin. Invest. 75:1023–1027.
Zaleznik et al. (1984), "Cellular Immune Mechanisms in Experimental Gram–Negative Sepsis" Abstract, Meeting of the American Society of Microbiology.
Finberg et al. (1985), "Suppressor T Cell Hybridoma Factor Prevents Abscesses".

Primary Examiner—Margaret Moskowitz
Assistant Examiner—D. Bernstein

[57] ABSTRACT

A method of protecting a mammal against a pathogenic bacterium by administering a soluble suppressor T-cell factor derived from a mammal that has been immunized with the bacterium or an antigenic surface fragment of the bacterium. Also disclosed are a hybrid cell fusion of an immunized suppressor T cell, methods of making such cells, and method of producing soluble suppressor T-cell factors.

5 Claims, No Drawings

ANTI-BACTERIAL T-CELL FACTOR

This invention was made during the course of work supported at least in part by NIH grant #AI-18796-02 and U.S. Army Medical Research and Development Command grant DAMD 17-83-C-3239; the U.S. Government has rights in this invention.

This is a continuation of co-pending application Ser. No. 741,232 filed on June 4, 1985 now abandoned.

BACKGROUND OF THE INVENTION

This invention relates to protecting against bacterial infection.

Traditional immunological models posit two classes of immune response: 1) the cellular immune responses mediated by lymphocytes designated as T cells which act directly against foreign matter or which activate macrophages to act against foreign matter; and 2) the humoral immune response initiated by a second class of lymphocytes designated as B cells. The cellular response involves direct attack by sensitized T cells on the invading antigen, e.g., attack on the surface of a foreign cell resulting in cell lysis. The humoral response involves secretion of antibodies by sensitized B cells. There are several other types of T cells in addition to the above-described cytotoxic T cells, including T cells that aid B-cell differentiation and proliferation (helper T cells), T cells that amplify cytotoxic T cells ($T_A$ cells), and T cells that suppress immune responses (suppressor T cells).

Much attention has been paid to antibody production by B cells, and it has become standard practice to generate antibodies to a selected antigen using hybrid cells made by fusing a sensitized B cell to a myeloma cell (B cell tumor line) that confers immortality on the hybrid.

It has also been known that an immune protection to pathologic bacteria or characteristic surface features of such bacteria can be transferred from one individual or species to another.

Ziegler et al. (1982) N.E. J. Med. 307:1225–1230 report treating human patients with human antiserum to bacterial endotoxin (lipopolysaccharide) prepared by vaccinating humans with heat killed *Escherichia coli* J5, a mutant having a core identical to most gram negative bacteria and lacking lipopolysaccharide oligosaccharide side chains.

An immune response to the capsular polysaccharide of *Bacteroides fragilis* protects against abscess formation caused by that organism. That immune response is reported to be cellular in nature, rather than humoral, and the cells that mediate the response are reportedly antigen-specific but non-H-2-restricted T cells belonging to the Ly-1−2+ subset, a subset which would not be expected to include helper T cells. Shapiro et al. (1982) J. Exper Med. 154:1188–1197. Thus, Shapiro et al. say (at pp. 1195) that It is not known how the protective effect against *B. fragilis* abcesses is mediated, but antibody production does not appear to play a decisive role . . . One might speculate that the immune T cell population is composed of suppressor cells . . . [A]nother possible interpretation is that T cells prevent the bacteria from becoming established at all . . . [An effector] T cell could function by binding or inactivating the bacteria or (more likely) by releasing a lymphokine that activates or attracts macrophages.

The protection against *B. fragilis* can be passively transferred by nylon wool non-adherent spleen cells. Onderdonk et al. (1982) J. Clin. Invest. 69:9–16.

Suppressor T cells are known to produce soluble factors specific for molecular antigens, and those soluble factors interact with other cells to control an immune response. Asherton et al. (1982) Annals. N.Y. Acad. Sci. Vol. 392:71-89. Healy et al. (1983) J. Immunology 131:2843–2847 disclose a suppressor T-cell hybridoma. Lifshitz et al. disclose a helper T-cell factor (1983) Proc. Nat'l Acad. Sci. 80:5689–5693. Murphy et al. (1983) J. Immunol. 130:2876–2881 disclose a soluble factor produced by antigen-specific suppressor T cells.

SUMMARY OF THE INVENTION

We have discovered that suppressor T cells produce a water soluble protein factor in response to a challenge by a bacterium or characteristic antigenic surface components of that bacterium. The protein factor conveys specific protection against the challenging bacterium when transferred as a soluble suppressor T-cell lysate or purified fraction thereof.

In one aspect, the invention features a method of protecting a mammal against a pathogenic bacterium by administering a water-soluble suppressor T-cell factor derived from a mammal that has been immunized with the bacterium or an antigenic surface fragment of the bacterium.

In a second aspect, the invention features: a hybrid cell comprising a fusion of a suppressor T cell from such an immunized organism; soluble factors and methods of treatment using such hybrid cells; and methods of making such hybrid cells.

In a third aspect, the invention features a soluble protein factor that confers immunity against *B. fragilis*-induced abscesses, the factor being characterized by: a) a molecular weight below 12,000; b) elution from a P2 Biogel column in fractions intermediate between the bed volume and the void volume using 4° C. 5mM $NH_4CH_3COO^-$ at pH 7.1, 8 cc/hour; and c) heat lability.

In preferred embodiments of the first two aspects, the bacterium is a member of the species *E. coli* or *B. fragilis*. The *B. fragilis* protection is provided by organisms immunized with the capsular polysaccharide of that bacterium.

The immune mechanism at work here is distinct from humoral immune mechanisms in that the factors are distinct from antibodies in their source (T cells, not B cells), their size (much smaller), and their structure (the absence of the large constant region characteristic of antibodies). The factors are also distinct from relatively non-specific protective T-cell products such as lymphokines or interferons. Finally, the factors are present in a cell lysate and are derived from suppressor T cells, thus distinguishing them from cellular immune response by cytotoxic T cells.

Other features and advantages of the invention will be apparent from the following description of the preferred embodiment.

DESCRIPTION OF THE PREFERRED EMBODIMENT

The anti-bacterial T-cell factor is illustrated by the following description of an anti-*B. fragilis* factor.

*Bacteriodes fragilis*, an extracellular gram negative anaerobe accounting for the majority of positive anaerobic blood cultures, is a common isolate from intraabdominal abscesses, particularly abscesses arising from a colonic source.

A cell-free factor (ITF) prepared from an immune splenic T-cell population protects from development of intraabdominal abscesses caused by *B. fragilis*. The active material is low in molecular weight, selectively binds to *B. fragilis* capsular polysaccharide, and induces antigen-specific immunity to abscesses. The material is heat-labile and loses efficacy after protease, but not nuclease, digestion.

Preparation of ITF

ITF is prepared by immunizing C57BL6 mice (Jackson Laboratory, Bar Harbor, Me.) at 6-10 weeks of age with capsular polysaccharide (CP) antigen of *B. fragilis* (ATCC accession number 23745, American Type Culture Collection, Rockville, Md.). CP antigen preparation is described in Kasper et al. (1983) J. Bacteriol. 153:991-997. Mice are immunized with 10 mg of antigen in 0.1 ml phosphate buffered saline (PBS) three times/week for three weeks.

At the fourth week, spleens from immunized mice are removed by blunt dissection, gently teased apart, and ground over a wire mesh screen. Cell suspensions in balanced salt solution (BSS) with 5% fetal calf serum (FCS) (M. A. Bioproducts, Walkersville, Md.) are counted by trypan blue dye exclusion after filtering through glass wool. Nylon wool columns are utilized to eliminate B cells and macrophages and to obtain T-cell-enriched spleen cell suspensions using the general method described in Onderdonk et al., cited above.

Lysates of T-cell-enriched fractions from immunized mice are prepared by serial freeze-thawing of known concentrations of cells. Suspensions containing $2.5 \times 10^7$ cells/ml are shell-frozen with dry ice and alcohol and then transferred to a boiling water bath sequentially four times. Debris is filtered out by passage over glass wool, and the volume returned to starting volume with BSS and 5% FCS. 1 ml aliquots are stored at $-80°$ C. Microscopic examination of the solution should reveal no intact cells.

One ml of the lysate prepared from T cells from immunized mice (ITF) is placed into a 12,000 MW exclusion dialysis membrane (Arthur H. Thomas Co., Philadelphia, Pa.) and dialyzed at 4° C. against 10 ml of 5 mM ammonium acetate buffer, ph 7.1. Dialysis proceeds for 24 hours with two changes of the dialysate. The contents of the dialysis bag are removed and frozen immediately at $-80°$ C. The dialysate is pooled (30 ml total volume) and frozen at $-80°$ C.

One cc of ITF containing the equivalent of $5 \times 10^7$ cells/ml is fractionated on an S-200 column, .9 $\times$ 50 cm column (Pharmacia, Uppsala, Sweden). The buffer is phosphate buffered saline (PBS) pH 7.2 and the column is run at 4° C. at a speed of 8 cc/h. Fractions are read at 280, 260 and 210 nm in a spectrophotometer (Perkin-Elmer, Norwalk, Conn.) and pooled fraction peaks are collected. Three ml of active peaks are, in turn, loaded on a P2 Biogel (Bio-Rad, Richmond, Calif.) column, 1.6 $\times$ 90 cm (Amicon, Danvers, Mass.) and run at 4° C. in 5 mM ammonium acetate buffer pH 7.1 at a speed of 8 cc/h. The refractive index (RI) is monitored (Waters Assoc., Milford, Mass.), appropriate fractions are pooled, and testing is performed in mice.

Use of ITF

The factor's ability to protect selectively against *B. fragilis*-related abscesses is tested by injecting 0.1-0.2 cc of factor or column fractions into mice by the intracardiac (i.c.) route. After 24 hours, animals are challenged i.p. with *B. fragilis* or complex inocula containing *B. fragilis* at a concentration of $1 \times 10^6$ organisms. Organisms are mixed 50:50 v/v with sterile cecal contents from meat-fed rats as adjuvant. Animals are sacrificed six days later and examined for abscesses. Animals with one or more gross abscess containing polymorphonuclear leukocytes (PMN) by gram stain are scored as positive for abscesses. For the experiments with complex inocula, abscess contents are cultured and gram negative rods of differing colonial morphologies, usually 5-10 colonies per plate, are subcultured and identified using standard anaerobic identification procedures.

ITF at concentrations of $2.5-25 \times 10^6$ cell equivalents prevents the development of abcesses following challenge with viable *B. fragilis* to the same degree as $2.5 \times 10^6$ intact immune T cells. No protection is provided against organisms such as *B. distasonis* (ATCC 8503) or *Fusobacterium varium* (TVDL 37). Neither $2.5 \times 10^6$ nonimmune T cells or $25 \times 10^6$ cell equivalents of NITF, a factor prepared from such T cells, provide any protection. Even a dose of $0.25 \times 10^6$ cell equivalents of ITF provides a significant degree of protection compared to NITF. Crude factor prepared by lysing immune T cells leaving no cells intact by microscopic examination is as active as intact cells in preventing abscess formation in mice. Protective ITF is prepared from mouse splenic T cells at least 46 days following completion of the immunization protocol.

Specificity of ITF

ITF's specificity for *B. fragilis* can be demonstrated not only by its failure to confer protection against other bacteria but also by its selective binding to *B. fragilis* CP. To verify this characteristic of ITF, it is adsorbed with sheep red blood cells (SRBC) coupled with either *B. fragilis* capsular polysaccharide or an unrelated capsular polysaccharide.

The preferred capsular polysaccharide of either *B. fragilis* or type III group B *Streptococcus* (GBS) is extracted and purified and coupled to sheep red blood cells (SRBC) with chromium chloride by the general method of Baker et al. (1976) J. Exp. Med. 143:258-270. Purified capsular polysaccharides are added to 10% solutions of SRBC in the presence of 1% chromium chloride. After five minutes incubation at room temperature, cells are washed in saline. Coupling is confirmed by specific hemagglutination of sensitized RBC in microtiter plates by rabbit antisera raised to purified CP. ITF, prepared as above, is incubated with SRBC coupled to either CP or with SRBC alone at 4° C. for 30 minutes. SRBC concentrations are $5 \times 10^7$ and $2.5 \times 10^8$ cells for $2.5 \times 10^7$ cell equivalents of ITF. After 30 minutes incubation, SRBC are removed by centrifugation. $25 \times 10^6$ cell equivalents of ITF in 0.2 cc are transferred i.c. to naive mice. Mice are challenged as usual with *B. fragilis* 24 hours later.

Mice receiving unadsorbed ITF and ITF adsorbed with SRBC alone or SRBC coupled to GBS CP are protected against abscesses caused by *B. fragilis*. Mice receiving ITF adsorbed with SRBC coupled to *B. fragilis* CP develop abscesses. Thus, absorption of ITF with SRBC coupled to *B. fragilis*, but not to the unrelated polysaccharide, eliminates the protective effect of the factor indicating that ITF derived from immune splenic T cells is capable of specific binding to the *B. fragilis* CP.

Characterization of ITF

To assess an approximate molecular size of the component which confers protection, ITF is dialyzed in a 12,000 MW exclusion dialysis membrane for 24 hours at 4° C. against 5 mM ammonium acetate pH 7.1.

The active component of the lysate is smaller than 12,000 MW since the dialysis bag contents loses protective capacity, while the dialysate is protective despite a thirty-fold dilution from the initial volume of 1 ml.

The T-cell lysate is purified partially by molecular sieve chromatography. ITF is loaded initially on an S-200 column and pooled fractions tested for protective activity in mice. Protection is conferred by fractions near and at the bed volume of the column. A protective peak which elutes at 26 ml from the S-200 column (where 12 ml represented void volume and 43 ml bed volume) is placed on a P2 Biogel column. Two ml fractions from the P2 Biogel column are pooled as marked by an elution profile recorded by RI monitoring. The P2 Biogel column has an exclusion size of 1800 MW for proteins. Doses of 0.2 cc of these pooled fractions are transferred to mice which are challenged and examined for abscesses.

Mice given 0.2 ml of peaks intermediate between the bed volume and void volume are protected from abscess formation. The bed volume peak and void volume peak do not protect. Thus, on the P2 Biogel column, protective activity resides in column fractions intermediate between the void volume and bed volume.

Heating ITF to 37° C. or 56° C. for 30 minutes eliminates the protective effect. The extreme heat lability of column-purified ITF indicates that the active component was not antibody. DNase/RNase treatments do not alter protection, but both pronase and trypsin digestion, however, eliminate the protective effect of ITF against abscesses caused by *B. fragilis* (p. less than 0.001 compared to ITF), indicating that ITF is a protein or, alternatively, that activity depends on a protein co-factor.

T-Cell Hybridomas

As an alternative to producing ITF from suppressor T-cell lysate, a hybridoma is produced by fusing an immunized suppressor T cell with a transformed or malignant cell. For example, the T cell may be fused with a mouse thymoma cell (T cell tumor line BW ATCC No. 5147) according to techniques known in the art for making hybridomas to produce monoclonal antibodies. A suitable fusion technique that can be followed is reported in Taniguchi et al. (1980) Nature 283:227 et seq.

A hybridoma producing ITF is selected by first isolating a single cell using the limiting dilution technique described generally in Langhore et al. (1981) Immunological Methods 2:–221 et seq. and then screening. For example, an in vitro bacteriological assay can be used to screen cells; alternatively, an immunological screening technique using antibody directed to ITF can be used.

Such an ITF-producing hybridoma was deposited with American Type Culture Collection, 12301 Parklawn Drive, Rockville, Md. 20852, on May 14, 1985, and has the accession number HB 8004.

Other Embodiments

Other embodiments are within the following claims. For example, the invention can be used to provide protection against other pathogenic bacteria. For example, rats immunized with rough mutant J5 *Escherichia coli* are a source of suppressor T cells (splenic) that produce a soluble factor protecting against challenge by wild-type *E. coli*. The suppressor T cells producing ITF can be human cells, rat cells, or mouse cells.

What is claimed is:

1. A hybrid cell producing a water-soluble factor, wherein said factor protects against formation of abscesses caused by *Bacteroides fragilis* bacterium, said cell comprising a fusion product of:
   (1) a suppressor T cell from a mammal immunized with said bacterium or a capsular polysaccharide thereof; and
   (2) a thymoma cell.

2. The hybrid cell of claim 1 wherein said mammalian suppressor T cell is a rat or mouse cell.

3. The hybrid cell of claim 1 wherein said bacterium is from the species *B. fragilis*.

4. The hybrid cell of claim 1 wherein said thymoma cell is derived from cell line BW ATCC 5147.

5. The hybrid cell of claim 1 wherein said hybrid cell is identical to or subcloned from the deposit designated ATCC HB 8004.

* * * * *